US008318111B2

(12) United States Patent  (10) Patent No.: US 8,318,111 B2
Mingerink et al.  (45) Date of Patent: Nov. 27, 2012

(54) PACKAGING CLOSURES INTEGRATED WITH DISPOSABLE RFID DEVICES

(75) Inventors: Corey Benjamin Mingerink, Appleton, WI (US); Gary Fabian Madsen, Greenville, WI (US); Brian James Carey, Neenah, WI (US); Frederick Karl Ashenbrenner, Sherwood, WI (US); Michael Donald O'Shea, Neenah, WI (US)

(73) Assignee: Binforma Group Limited Liability Company, Dover, DE (US)

( * ) Notice: Subject to any disclaimer, the term of this patent is extended or adjusted under 35 U.S.C. 154(b) by 14 days.

(21) Appl. No.: 13/006,843

(22) Filed: Jan. 14, 2011

(65) Prior Publication Data
US 2011/0169614 A1 Jul. 14, 2011

Related U.S. Application Data

(63) Continuation of application No. 11/524,002, filed on Sep. 20, 2006, now Pat. No. 7,887,755.

(51) Int. Cl.
*B01L 3/14* (2006.01)
(52) U.S. Cl. ........ 422/550; 422/547; 422/549; 422/555; 422/556; 340/572.1; 206/459.5
(58) Field of Classification Search .................. 422/547, 422/549, 550, 555, 556; 206/205, 206, 216, 206/223, 459.5, 569; 340/571, 572.1, 572.3, 340/572.7, 572.8, 572.9
See application file for complete search history.

(56) References Cited

U.S. PATENT DOCUMENTS

| 5,566,441 | A | 10/1996 | Marsh et al. |
|---|---|---|---|
| 5,949,059 | A | 9/1999 | Rawson, Sr. et al. |
| 6,018,299 | A | 1/2000 | Eberhardt |
| 6,107,920 | A | 8/2000 | Eberhardt et al. |
| 6,392,544 | B1 | 5/2002 | Collins et al. |
| 6,395,373 | B2 | 5/2002 | Conti et al. |
| 6,404,643 | B1 | 6/2002 | Chung |
| 6,421,013 | B1 | 7/2002 | Chung |
| 6,478,229 | B1 | 11/2002 | Epstein |
| 6,481,631 | B1 | 11/2002 | Poustis |

(Continued)

FOREIGN PATENT DOCUMENTS
WO  WO-93/19993 A1  10/1993
(Continued)

OTHER PUBLICATIONS

Karjoth, G. And Moskowitz, P., "Disabling Rfid Tages with Visible Confirmation: Clipped Tags are Silenced," WPES '05 Proceedings of the 2005 ACM Workshop on Privacy in the Electronic Society, Alexandria, VA, Nov. 5, 2005, pp. 27-30.

(Continued)

*Primary Examiner* — Jill Warden
*Assistant Examiner* — Dwayne K Handy
(74) *Attorney, Agent, or Firm* — Perkins Coie LLP

(57) ABSTRACT

A packaging system (20), has a container (22) which delimits a container volume which can hold at least one unit-measure or unit-quantity of a selected commodity or article (24). The container includes at least one access portion (26) that can provide a selective closed arrangement and a selective open arrangement. An electronic data mechanism (28) can be operatively connected to the container (22), and can be operatively configured to electronically transpond or otherwise transmit data to a reader mechanism (30). A deactivation mechanism (32) can be operatively connected to the container (22) and to the electronic data mechanism (28), and can be operatively configured to selectively disable the electronic data mechanism.

12 Claims, 13 Drawing Sheets

U.S. PATENT DOCUMENTS

| | | | |
|---|---|---|---|
| 6,557,758 B1 | 5/2003 | Monico | |
| 6,667,092 B1 | 12/2003 | Brollier et al. | |
| 6,694,653 B2 | 2/2004 | Bradfield et al. | |
| 6,737,974 B2 | 5/2004 | Dickinson | |
| 6,750,769 B1 | 6/2004 | Smith | |
| 6,765,476 B2 | 7/2004 | Steele et al. | |
| 6,782,601 B2 | 8/2004 | Smeyak et al. | |
| 6,794,000 B2 | 9/2004 | Adams et al. | |
| 6,802,659 B2 | 10/2004 | Cremon et al. | |
| 6,859,745 B2 | 2/2005 | Carr et al. | |
| 6,888,509 B2 | 5/2005 | Atherton | |
| 6,951,596 B2 | 10/2005 | Green et al. | |
| 6,982,640 B2 | 1/2006 | Lindsay et al. | |
| 7,009,519 B2 | 3/2006 | Leonard et al. | |
| 7,032,816 B2 | 4/2006 | Markham et al. | |
| 7,034,689 B2 | 4/2006 | Teplitxky et al. | |
| 7,084,769 B2 | 8/2006 | Bauer et al. | |
| 7,095,324 B2 | 8/2006 | Conwell et al. | |
| 7,098,794 B2 | 8/2006 | Lindsay et al. | |
| 7,100,052 B2 | 8/2006 | Ghazarian | |
| 7,887,755 B2 * | 2/2011 | Mingerink et al. | 422/547 |
| 2001/0054755 A1 | 12/2001 | Kirkham | |
| 2002/0067264 A1 | 6/2002 | Soehnlen | |
| 2002/0188259 A1 | 12/2002 | Hickle et al. | |
| 2003/0061706 A1 | 4/2003 | Smeyak et al. | |
| 2003/0155415 A1 | 8/2003 | Markham et al. | |
| 2003/0235027 A1 | 12/2003 | Smeyak et al. | |
| 2004/0008613 A1 | 1/2004 | Beckwith et al. | |
| 2004/0100359 A1 | 5/2004 | Reade et al. | |
| 2004/0131897 A1 | 7/2004 | Jenson et al. | |
| 2004/0226904 A1 | 11/2004 | Schroeder | |
| 2005/0012616 A1 | 1/2005 | Forster et al. | |
| 2005/0037163 A1 | 2/2005 | Wu et al. | |
| 2005/0043158 A1 | 2/2005 | Wu et al. | |
| 2005/0127176 A1 | 6/2005 | Dickinson et al. | |
| 2005/0137940 A1 | 6/2005 | Lindsay | |
| 2005/0190914 A1 | 9/2005 | Chen et al. | |
| 2005/0242950 A1 | 11/2005 | Lindsay et al. | |
| 2006/0092014 A1 | 5/2006 | Onderko et al. | |
| 2007/0008121 A1 | 1/2007 | Hart | |
| 2008/0069736 A1 | 3/2008 | Mingerink et al. | |

FOREIGN PATENT DOCUMENTS

| | | |
|---|---|---|
| WO | WO-03/061060 A2 | 7/2003 |
| WO | WO-2005024745 A2 | 3/2005 |
| WO | WO-2007/073529 A2 | 6/2007 |

OTHER PUBLICATIONS

Lindsey, Jeffrey D., "Retail RFID Systems Without Smart Shelves," Article 21114D on IP.com, http://priorart.ip.com/viewPub.jsp?pubID=IPCOM000021114D, Dec. 23, 2003, 14 pgs.

Moskowitz, Paul A. et al., "Privacy-Enhancing Radio Frequency Identification Tag: Implementation of the Clipped Tag," White Paper, RFID Journal Live, May 2006, pp. 1-4.

O'Connor, M. "IBM Proposes Privacy Protecting Tag," http://www1.rfidjournal.com/articleprint/1972/-1/1/, RFID Journal, Nov. 7, 2005, pp. 1-3.

* cited by examiner

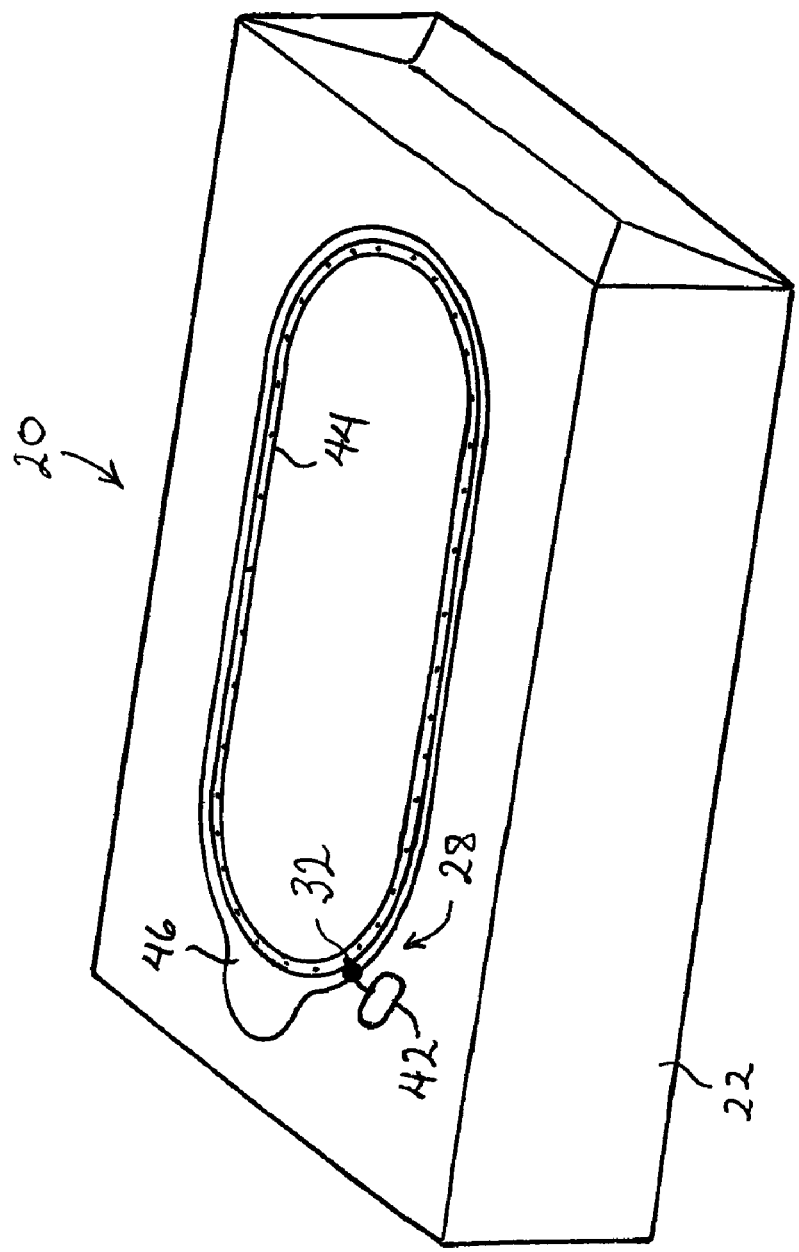

PACKAGING CLOSURES INTEGRATED WITH DISPOSABLE RFID DEVICES

CROSS-REFERENCE TO RELATED APPLICATION

This application is a continuation of U.S application Ser. No. 11/524,002 filed Sep. 20, 2006, now U.S. Pat. No. 7,887,755, which is incorporated herein by reference in its entirety.

TECHNICAL FIELD

The present invention relates to the field of article identification and data tracking. In particular configurations, the invention relates to a system for reading electronic data mechanisms.

BACKGROUND OF THE INVENTION

Data tag technology such as radio frequency identification (RFID) technology has employed passive smart tags (miniature antenna-containing tags requiring no internal power supply) that may be embedded in or attached to a product or material to convey information that may be read by a scanner or other interrogator device. Generally, conductive or passive smart tags include a data circuit and an antenna. In particular, smart tags include a semiconductor, a coiled, etched, or stamped antenna, a capacitor, and a substrate on which the components are mounted or embedded. A protective covering is typically used to encapsulate and seal the substrate. Other data mechanisms have been configured to be active or semi-passive.

In general, RFID systems and other data mechanism systems include readers and tags in which the tags generate an electromagnetic response to an electronic signal from a reader. The response signal is read by the reader, typically with a readable range on the order of a few feet, though broader or narrower ranges are possible. The signal generated by the tag includes information (e.g., an electronic product code) that identifies the tag or the product comprising the tag.

The data tags have typically been intended for use during manufacturing, marketing, inventory and sales operations. After the intended use, the consumers of the tagged articles have desired a convenient technique for destroying or otherwise disabling the ordinary operation of the data tag. The disabling of the data tag has been excessively difficult or has excessively modified the appearance of the associated product. As a result, there has been a continued need for techniques and devices that can more conveniently or more selectively disable a data tag. There has also been a continued need for techniques and devices that can more conveniently or more selectively re-enable the disabled data tag.

BRIEF DESCRIPTION OF THE INVENTION

A packaging system has a container which delimits a container volume which can hold at least one unit-measure or unit-quantity of a selected commodity or article. The container includes at least one access portion that can provide a selective closed arrangement and a selective open arrangement. An electronic data mechanism can be operatively connected to the container, and can be operatively configured to electronically transpond or otherwise transmit data to a reader mechanism. A deactivation mechanism can be operatively connected to the container and electronic data mechanism, and can be operatively configured to selectively disable a significant portion of the electronic data mechanism. In a particular aspect, the data mechanism may be selectively reactivated.

The system can provide a convenient technique for destroying or otherwise disabling the ordinary operation of the data mechanism. The system can more conveniently or more selectively disable the electronic data mechanism, and the disabling of the data mechanism can be obtained without excessively modifying the appearance of the associated package or other associated product or component. In particular arrangements, the data mechanism may be selectively reactivated to provide additional information regarding the status of an associated product.

BRIEF DESCRIPTION OF THE DRAWINGS

The method and apparatus will be better understood by reference to the following description of the method and apparatus taken in conjunction with the accompanying drawings, wherein:

FIG. 9 shows a perspective view of a representative container, which includes a box and a flap-closure mechanism that can be selectively moved to open and close the box, and where the container is in a closed condition.

Corresponding reference characters indicate corresponding parts throughout the drawings.

DETAILED DESCRIPTION OF THE METHOD AND APPARATUS

When introducing elements of the present method and apparatus or the particular configurations thereof, the articles "a," "an," "the," and "said" are intended to mean that there are one or more of the elements. The terms "comprising," "including," and "having" are intended to be inclusive and mean that there may be additional elements other than the listed elements. Accordingly, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

An electronic data tag, smart tag, or other electronic data mechanism may be placed by hand or by machinery on a package, or on another appointed product or component that is associated with the data mechanism. The data mechanism may, for example, be placed inside or outside of the product and/or package. The electronic data mechanism may or may not be a separately provided item or component, relative to its associated product or component. In a particular feature, the data mechanism can store identification information. In one aspect, the information in the tag can be used to assist in a routing of an individual product during the manufacturing process. Additionally, the information in the data mechanism can be utilized during the distribution, marketing, intermediate use and/or end use of the package, or other appointed product or component.

Figure 1:
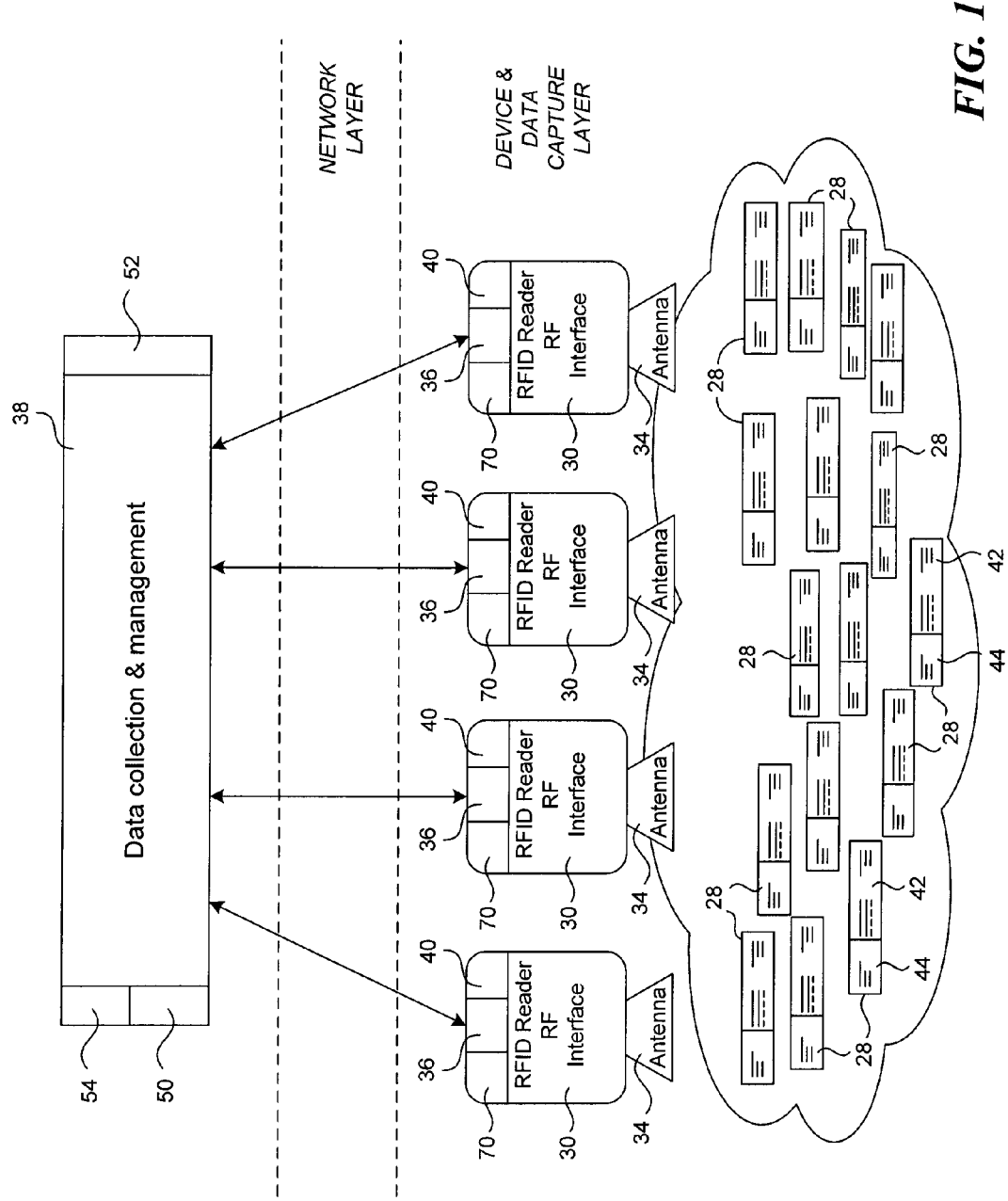
FIG. 1 shows an exemplary block diagram of a system which includes at least one device for reading one or more electronic data mechanisms.

Referring to FIG. 1, a representative system for reading the electronic data tag or other electronic data mechanism 30 can include at least one individual reader mechanism 30. Each individual reader 30 can have an operative power supply 70, at least one reader antenna 34, and a communication system 36 for relaying data from the individual reader to an electronic data collection and management system 38. The reader may also include or may otherwise be operatively connected to a computerized electronic processor 40. The electronic processor can, for example, implement a programming of protocols for each reader 30 and its corresponding reader antenna 34. In a particular aspect, the electronic processor can provide any needed digital signal processor (DSP) logic and protocol code to an individual reader. In other aspects, the reader system can include a plurality of two or more individual readers 30, and each reader can include a plurality of individual reader antennas.

The reader mechanism 30 can typically be arranged and configured to interrogate an electronic tag or other electronic data mechanism that has been affixed or otherwise operatively connected to a package or other container. The reader mechanism can be configured to be operable with any cooperating form of the electronic data mechanism 28 including, but not limited to, a smart tag and an active, semi-passive, or passive radio frequency identification (RFID) tag or the like, as well as combinations thereof.

RFID technology (e.g. smart tag technology) is known and understood by those skilled in the art, and a detailed explanation thereof is not necessary for purposes of describing aspects of the present method and apparatus. RFID systems for improved manufacturing have been proposed for systems including the PIPE/STORM systems disclosed in commonly owned U.S. patent application Ser. No. 10/306,794, "Communication Between Machines and Feed-Forward Control in Event-Based Product Manufacturing," filed Nov. 27, 2002 (U.S. Patent Application Publication 2003/0155415; dated Aug. 21, 2003) by Markham et al., which is incorporated herein by reference in a manner that is consistent (noncontradictory) herewith.

In general, electronic data mechanisms (e.g. RFID chips) can include read-only devices (e.g. read-only chips), which include a fixed electronic code. Alternatively, the electronic data mechanisms (e.g. RFID chips) may be read-write devices (e.g. read-write chips), which allow an updating of prior information or an addition of new information. The devices may also be associated with sensors to read detected information and transmit a signal responsive to the detected information, such as a value detected from a biosensor. Exemplary smart tags that include RFID technology associated with a sensor are the active labels that are commercially available from KSW MICROTEC (Dresden, Germany). For example, TEMPSENS active smart labels can measure and record temperature.

RFID devices or tags can take many physical formats, such as a microchip from 30 to 100 microns thick and from 0.1 to 1 mm across, joined to a minute metal antenna such as the Hitachi 2.45 GHz Mew chip. Another form is the "Coil-on-Chip" system from Maxell (Tokyo, Japan). Exemplary RFID vendors of tags and/or readers and associated systems include Intermec Technologies Corporation (Everett, Wash.), Symbol Technologies (Holtsville, N.Y.), Applied Wireless Identifications, Inc. (AWID) (Monsey, N.Y.), Philips Semiconductor (Eindhoven, The Netherlands), and Texas Instruments (Dallas, Tex.).

A reader 30 may be integrated into or added onto a laptop, a personal data assistant (PDA) device, a cellular telephone, or other electronic device. Readers for use in the present method and apparatus may include any known variety, including multi-protocol readers (e.g., those of Applied Wireless Identifications, Inc.) that scan multiple frequencies or that are adapted for reading a variety of RFID tags or other identification elements. Data mechanism readers may also be adaptive readers that adjust their scanning frequency, signal strength, and/or signal orientation or direction to improve the signal obtained from the tag or tags being read. Readers that can adapt their frequency are discussed, by way of illustration, in U.S. Pat. No. 6,765,476, "Multi-level RF Identification System," issued Jul. 20, 2004 to Steele, herein incorporated by reference in a manner that is noncontradictory herewith.

Each individual reader 30 can have an operative power supply, and at least one antenna 34. Optionally, the individual reader may include an antenna group or set having a plurality of antenna 34. Multiple antennas can, for example, help the reader interrogate and receive data from a diverse selection of tags (or other electronic data mechanisms) where the individual tags have been configured to operate in different, widely-spaced frequencies or frequency bands, such as low-frequency (LF), high-frequency (HF), very-high frequency (VHF), ultra-high frequency (UHF) and super-high frequency (SHF). The operational radio-frequency of the various components of the reader system (e.g. readers, antennas, communication systems) can be as low as about 100 KHz (kilo-Hertz), and can be up to about 6 GHz (Giga-Hertz), or more.

The reader and/or its antenna system may be powered by conventional techniques and devices. Such techniques and devices can, for example, include capacitors, batteries, photovoltaic cells, electrically-wired power supplies or the like, as well as combinations thereof. Optionally, the reader 30 and/or its antenna 34 may be powered by a Power-Over-Ethernet (POE) system.

The system of the present disclosure may be configured to operatively cooperate with a portal unit through which packages or other product can pass and be subjected to scanning or other interrogation. The portal unit can include one or more data mechanism readers (e.g., scanners, transponders, interrogators, or antenna systems). For example, RFID portals for forklifts, pallets, and other loads are well known, such as the portals of Pelican Control Systems Ltd. (England) and that of U.S. Patent Publication 20020104013, "Electronic Vehicle Product and Personal Monitoring." Examples of other RFID portals include the LEADS-TRAKKER portal for reading RFID tags on humans, such as guests at conventions wearing RFID-enable passes. Automated tollbooths using RFID scanners are also another form of portal within the scope of the present method and apparatus.

The system may also be configured to operatively cooperate with self-adjusting portals, in which the physical location of readers in an individual portal are adjusted to optimize the read of an approaching load. Examples of such portals are described in U.S. patent application Ser. No. 10/976,993 entitled "SELF-ADJUSTING PORTALS WITH MOVABLE DATA MECHANISM READERS FOR IMPROVED READING OF DATA MECHANISMS" by John Onderko et al. and filed Oct. 29, 2004; the entire disclosure of which is incorporated herein by reference in a manner that is consistent herewith.

Figure 2:
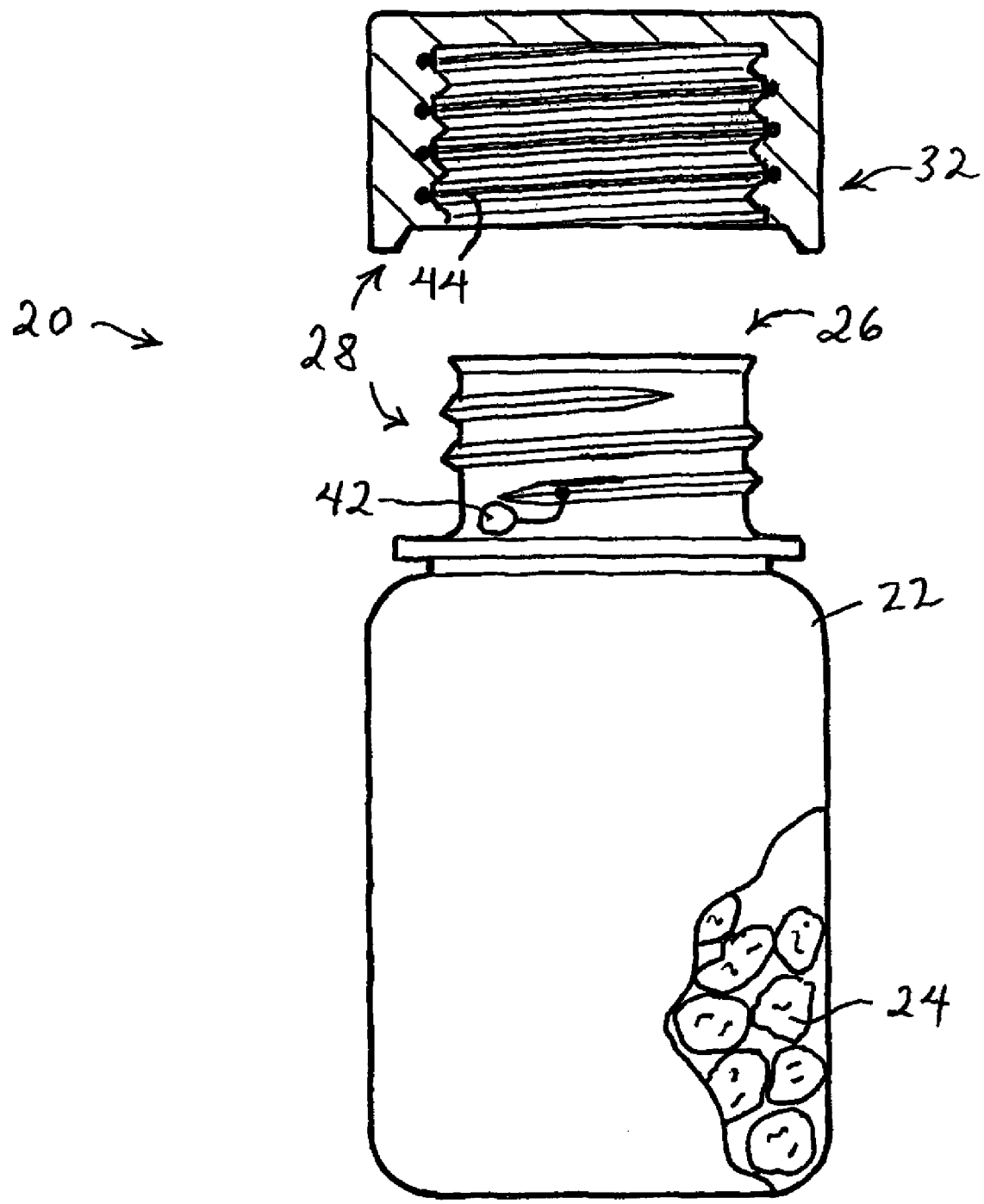
FIG. 2 shows a partially cut-away and partially-sectioned, side view of a representative container for holding one or more commodity items, where the container includes a bottle and a screw-on cap, and the container is in an open condition.

Referring to FIG. 2, for example, a packaging system 20 has a container 22 which delimits a container volume, and the container volume can operatively hold at least one unit-measure or unit-quantity of a selected commodity or article 24. The container includes at least one access portion 26 that can provide a selective closed arrangement and a selective open arrangement. An electronic data mechanism 28 can be operatively connected to the container 22, and can be operatively configured to electronically transpond or otherwise transmit data to a reader mechanism 30. A deactivation mechanism 32 can be operatively connected to the container 22 and to the electronic data mechanism 28, and can be operatively configured to selectively disable at least an operationally significant portion of the electronic data mechanism. Desirably, the electronic data mechanism can be operatively disabled from performing a substantial entirety of its previously intended, ordinary operation. In a particular aspect, the deactivation mechanism 32 can be operatively configured to temporarily disable the previous, ordinary operation of the electronic data mechanism. In another aspect, the packaging system can include a reactivation mechanism which is configured to selectively re-enable the electronic data mechanism in an operative configuration.

By incorporating its various aspects and features, alone or desired combinations, the packaging system 20 can provide a convenient technique for destroying, disabling or otherwise deactivating the ordinary operation of the data tag or other electronic data mechanism. The system can more conveniently or more selectively disable an electronic data mechanism, and the disabling of the data mechanism can be obtained without excessively modifying the appearance or operation of the associated package or other associated product or component. The system can also help reduce consumer privacy concerns, and provide desired interactions with other "smart" devices. For example, the system can provide desired interactions with inventory control systems.

The container 22 can operatively delimit an interior container volume by incorporating any operative configuration, and any suitable container may be employed. For example, the container may include a pouch, carton, box, can, bottle, jar, bag, blister-pack or the like, as well as combinations thereof.

The container volume can operatively hold at least one unit-measure or unit-quantity of a selected commodity or article 24. It should be readily appreciated that any suitable article or other commodity may be employed. For example, the selected article or commodity may include a liquid, solid, gel, powder, food item, non-food item, compressed item or the like, as well as combinations thereof.

The container includes at least one access portion 26 that can provide a selective closed arrangement (e.g. FIGS. 3 and 5) that operatively prevents access to the contained items, and a selective open arrangement (e.g. FIGS. 2 and 7) that operatively allows access to the contained items. As representatively shown in FIG. 9, for example, a suitable access portion can include an access flap 46. A suitable access portion can alternatively include an access lid 48 (e.g. FIG. 11). In a particular aspect, the access portion can include a screw-on, access lid (e.g. FIG. 2). In other arrangements, the access portion may include a zipper mechanism (e.g. a ZIPLOK mechanism) (e.g. FIG. 7), or a closure tab (e.g. FIG. 4).

The electronic data mechanism 28 can be operatively connected to the container 22, and can be operatively configured to electronically transpond or otherwise transmit data to a cooperating reader mechanism 30. In a desired arrangement, the electronic data mechanism can be a RFID tag. Additionally, the RFID tag or other electronic data mechanism can include a data memory portion 42 and a tag antenna portion 44. During ordinary, intended operation, the data memory portion is operatively connected to the tag antenna portion. For example, the data memory portion 42 can be mechanically or electronically coupled to the tag antenna portion 44. In a particular arrangement, the data memory portion 42 of the electronic data mechanism can be operatively connected to the access portion 26 of the container 22, and the tag antenna portion 44 of the electronic data mechanism can be operatively connected to a section of the container that is operatively spaced from the access portion. Alternatively, the antenna portion 44 of the electronic data mechanism can be operatively connected to the access portion 26 of the container, and the data memory portion 42 of the electronic data mechanism can be operatively connected to a section of the container 22 that is operatively spaced from the access portion.

In a particular feature of the system 20, a deactivation mechanism 32 can be operatively connected to the container 22 and electronic data mechanism 28. The deactivation mechanism can be operatively arranged and configured to selectively disable at least a significant portion of the electronic data mechanism. In a particular arrangement, the electronic data mechanism can be operatively disabled from performing a significant portion of its previously intended, ordinary operation. Desirably, the electronic data mechanism may be operatively disabled from performing a substantial entirety of its previously intended, ordinary operation. The disablement may be configured to be substantially permanent. Alternatively, a particular aspect can have a deactivation mechanism 32 which is operatively configured to temporarily disable the previous, ordinary operation of the electronic data mechanism.

The disabling of the electronic data mechanism can be provided by any operative technique or mechanism. The disabling may include an electronic operation, a mechanical operation or the like, as well as combinations thereof. For example, the disabling can include an electronic disconnection that is operatively disabling. Alternatively, the disabling may include a non-electronic disconnection, a mechanical disconnection or other non-electronic disabling configuration. For example, the deactivation mechanism may be configured to mechanically disconnect the data memory portion from the antenna portion.

In a particular arrangement, the deactivation mechanism may be configured to selectively disconnect the data memory portion 42 from the antenna portion 44 of the electronic data tag or other electronic data mechanism. For example, the deactivation mechanism can be configured to manually disconnect the data memory portion 42 from the antenna portion 44 of the electronic data mechanism. Thus, the deactivation mechanism can be configured to allow a convenient, manual disabling of the electronic data mechanism by an ordinary user. The disabling can, for example, be provided by an operationally significant reduction in the range or distance at which the electronic data mechanism 28 can effectively be interrogated by and effectively be responsive to a cooperating, electronic reader 30.

In another aspect, the packaging system 20 can include a reactivation mechanism which is configured to selectively re-enable the electronic data mechanism 28 in an operative configuration. Accordingly, a significant portion of the ordinary operation of the electronic data mechanism can be selectively disabled and then re-enabled one or more times. The reactivation mechanism can be configured to re-enable the electronic data mechanism to an ordinary operative configuration. Thus, the electronic data mechanism can be substantially restored to a previous condition of ordinary operation. Desirably, the reactivation mechanism can be configured to selectively re-enable a previously disabled portion of the electronic data mechanism. For example, the reactivation mechanism can be configured to selectively reconnect the data memory portion 42 to its associated, cooperating antenna portion 44 in an operative configuration.

In a particular feature, the reactivation mechanism can be configured to selectively reconnect the data memory portion 42 to the cooperating antenna portion 44 with an operative mechanical connection. Alternatively, the reactivation mechanism can be configured to selectively reconnect the data memory portion 42 to the tag antenna portion 44 with an electronically-coupled or other operative, non-mechanical connection. A particular arrangement can have the deactivation mechanism configured to manually reconnect the electronic data mechanism. Thus, the deactivation mechanism can be configured to allow a convenient, manual re-enabling of the electronic data mechanism by an ordinary user.

Another aspect of the packaging system 20 can include a reader mechanism 30 that is operatively connected to a first counter 50, and the first counter can be configured to operatively record a number of times that a deactivation mechanism has been operated. A further aspect of the packaging system 20 can include a reader mechanism 30 that is operatively connected to a timer 52 which can operatively provide for a determination of a number of times that the deactivation mechanism is operated during a predetermined time period. In still another aspect, the packaging system 20 can include a reader mechanism 30 that is operatively connected to a second counter 54 which can operatively record a number of times that the reactivation mechanism has been operated.

In a particular aspect, the first counter may be configured to record the number of times that the deactivation mechanism on a particular category of containers has been operated. For example, each container may correspond to a single-use article. Thus, each operation of a deactivation mechanism can be employed to correlate a reduction in a previous inventory of the single-use article.

In another aspect, the first counter may be configured to record the number of times that the deactivation mechanism on a single, individual container has been operated. For example, the first counter may be configured to record the number of times that the deactivation mechanism on a single, individual container has been operated by opening the access portion of the container from a previously closed condition. Where each opening and/or re-closing of the single container can be correlated to a particular decrease in the amount of the article or commodity held in the container, and where the initial amount of the commodity is known, one can use the counter information to at least approximately determine a remaining amount of the commodity in the single container.

Information and data regarding the operative deactivation and/or reactivation of the electronic data mechanism 28 can also be employed to help perform one or more tasks, such as inventory control, privacy control, product usage or the like.

In the various arrangements of the packaging system 20, the employed counter (e.g. first counter 50 and/or second counter 54) can include any operative counting device or technique. For example, an individual, employed counter may include a mechanical counter. Desirably, the individual, employed counter can include a non-mechanical or electronic counter. Similarly, the various arrangements of the packaging system 20 can include any operative timing device or technique. For example, an individual, employed timer may include a mechanical timer. Desirably, the individual, employed timer can include an electronic or other non-mechanical timer.

The individual, employed counter (50, 54) and/or the individual, employed timer may have any operative location. For example, the individual counter and/or timer may be positioned in the reader mechanism 30. Alternatively, the individual counter and/or timer may be positioned in the cooperating, electronic data collection and management system 38, as desired.

The communication system 36 can be configured to operatively relay information and data from the individual reader to an electronic data collection and management system 38. The communication system can be wired, wireless or a combination thereof. Suitable communication systems are conventional and available from commercial vendors.

The communication system 36 can be configured to include a personal data assistant (PDA) device, a cellular phone, a laptop computer or the like, as well as combinations thereof.

The electronic data collection and management system 38 can, for example, include a computer network or a computerized database. Other examples of a suitable electronic data collection and management system can include software, techniques and/or devices regarding inventory control, product development information, and/or marketing information.

The computerized electronic processor 40 is ordinarily located in the employed reader, and can be operatively configured to implement a programming of protocols for each individual reader 30 and its cooperating reader antenna or antennas 34.

The signals received by the reader antenna from readings (e.g. from backscatter readings) or other detections of information from cooperative data mechanisms (e.g. RFID tags) can be sent to the electronic data collection and management system 38 over an operative communication link, such as a wired or wireless network, and the signals can be analyzed, interpreted and processed by the data collection and management system. For example, the electronic data collection and management system 38 can be operatively coordinated with a cooperating, warehouse system, or may be operatively integrated with any other software system. Such software systems can, for example, include Enterprise Resource Planning (ERP) systems, or the like.

Information from the electronic data collection and management system 38 can be employed to provide selected functions. Such functions can, for example, include inventory control, production forecasting, marketing analyses, process improvement or the like, as well as combinations thereof.

The electronic data collection and management system 38 can be cooperatively coordinated with other selected systems. In a desired aspect, the electronic data collection and management system 38 can be cooperatively coordinated with a computerized home-management system. The computer-controlled, home-management system can provide risk/safety assessments, expiration control or the like, as well as combinations thereof.

The reader system may operatively connect multiple "smart" antennas 34 to an individual computerized electronic processor 40 (e.g. computer server). In particular arrangements, for example, each antenna may be remotely activated for a period of time to provide readings without interference from the other antennas so networked. In another arrangement, the communication between the server and multiple antennas may incorporate the principles of the smart shelf system of MeadWestvaco Intelligent Systems (now Vue Technologies), in which a single reader communicates with multiple antennas using systems analogous to computer network communications protocols. Such a system is described in WO2003061060A2 of MeadWestvaco Intelligent Systems (now Vue Technology).

In further configurations of the reader system, some degree of logic may still be programmed into the antenna. In particular arrangements, the power delivered to the antennas by the network can be responsive to feed-forward information provided by other devices that may scan or otherwise interrogate a code on a pallet, for example, and the scanned code can provide information about the optimum reader power to read data tags associated with individual items on the pallet.

RFID may be applied in various ways to determine a location of the article 102. This can be done, for example, using triangulation involving a plurality of RFID readers that read the tag, or with directional readers that scan for the location of a tag. See, for example, J. Lindsay, "RETAIL RFID SYSTEMS WITHOUT SMART SHELVES," published at IP.com as Document 21114D, Dec. 23, 2003, herein incorporated by reference. A directional reader with a directional and optionally moveable antenna or antenna array adapted to determine the approximate location of an RFID tag may be mounted on or near the positioning device 106, or remote therefrom, or may be the data mechanism reader 104 itself of FIG. 1. One example of a reader system adapted for determining the spatial location of a tag is taught by D. G. Bauer et al. in "INTELLIGENT STATION USING MULTIPLE RF ANTENNAE AND INVENTORY CONTROL SYSTEM AND METHOD INCORPORATING THE SAME," U.S. Patent Publication 200030174099-A1, published Sep. 18, 2003, filed as U.S. patent application Ser. No. 10/338,892, assigned to MeadWestvaco Corporation, herein incorporated by reference in a manner that is noncontradictory herewith. Another approach is described in U.S. Pat. No. 6,750,769, "METHOD AND APPARATUS FOR USING RFID TAGS TO DETERMINE THE POSITION OF AN OBJECT," issued Jun. 15, 2004 to R. B. Smith, herein incorporated by reference in a manner that is noncontradictory herewith. The system described in U.S. Pat. No. 6,750,769 employs an array of RFID tags, some of which are obscured relative to a reader by the presence of an intervening object. Analysis of the obscured and non-obscured signals provides spatial information about the object.

The packaging system can be operated with any form of computer or computing device known in the art. A user may enter commands and information into the computing device through input devices or user interface selection devices well known in the art such as a keyboard and a pointing device (e.g., a mouse, trackball, pen, or touch pad). The computer typically has at least some form of computer readable media. Computer readable media, which include volatile and non-volatile media, removable and non-removable media, may include any available medium that may be accessed by a computer. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information and that may be accessed by the computer. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection; and wireless media, such as acoustic, RF, infrared, and other wireless media, are examples of communication media. Combinations of any of the above are also included within the scope of computer readable media. The packaging system may also include the computing device itself when programmed and configured in accordance with the methods and techniques described in the present disclosure.

The packaging system may be employed in the general context of computer-executable instructions, such as program modules, executed by one or more computers or other operative devices. Generally, program modules can include, but are not limited to, routines, programs, objects, components, and data structures that perform particular tasks or implement particular abstract data types. The method and apparatus may also be practiced in distributed computing environments where tasks are performed by remote processing devices that are linked through a communications network. In a distributed computing environment, program modules may be located in both local and remote computer storage media including memory storage devices.

A related technology within the scope of the present method and apparatus is Surface Acoustic Wave (SAW) technology. For example, InfoRay (Cambridge, Mass.) markets a passive smart tag that is said to achieve long ranges (up to 30 meters) using a Surface Acoustic Wave (SAW) device on a chip coupled with an antenna. The SAW device converts a radio signal to an acoustic wave, modulates it with an identification code, then transforms it to another radio signal that is emitted by the smart tag and read by a scanner or other reader. The identification code of the smart tag is extracted from the radio signal. RFSAW, Inc. (Dallas, Tex.) also provides highly miniaturized, Surface Acoustic Wave (SAW) RFID devices that may be used within the scope of the present method and apparatus.

Another related technology is ultra-wide band (UWB) technology. UWB technology permits wireless communication between objects using low-power electromagnetic transmissions. However, the receivers and transmitters generally are both active, but use very low power, typically less than that of radio frequency noise, relying on transmissions of intermittent pulses over a broad band of frequencies rather than transmissions limited to a particular frequency. UWB technology may provide much higher spatial capacity (information transmission per unit area) than other wireless standards such as BLUETOOTH brand computer communication services, or Institute of Electronics and Electrical Engineering (IEEE) 802.11a or 802.11b communication systems.

The following, representative configurations of the invention are presented to provide a more detailed understanding of the invention. The representative configurations are not intended to limit the scope of the present invention in any way. From a complete consideration of the entire disclosure, other arrangements within the scope of the claims will be readily apparent to one skilled in the art.

With reference to FIG. 2, the packaging system can have a container 22 configured to provide a bottle with a threaded opening region. The bottle has an access portion 26 which includes an access opening that is generally adjacent one end of the bottle, and a cooperating cap. Desirably, the bottle can have a neck region that can be threaded to accept a set of cooperating threads operatively located on the bottle cap. Thus, the cap can be installed to provide the selective, closed arrangement, and can be removed to provide the selective, open arrangement of the access portion. The electronic data mechanism 28 can include a data memory portion 42 and a tag antenna portion 44. In a desired arrangement, the data mechanism can be a RFID tag. The data portion 42 can be connected to any operative section of the bottle container 22, and as representatively shown, the data portion may be attached to the main body of the bottle, and positioned proximate the opening section of the bottle. The antenna portion 44 can be connected to the cap and is appropriately configured to provide the desired antenna functionality. When the cap is installed, the antenna portion 44 operatively connects to the data portion 42 of the electronic data mechanism, and the electronic data mechanism can be configured in an enabled condition. When the cap is removed, the antenna portion 44 operatively disconnects from the data portion 42 to thereby disable the previous, ordinary operation of the electronic data mechanism. When the cap is replaced, the antenna portion 44 operatively reconnects to the data portion 42 to thereby re-activate or otherwise re-enable the RFID tag or other electronic data mechanism to its intended operation.

Figure 3:
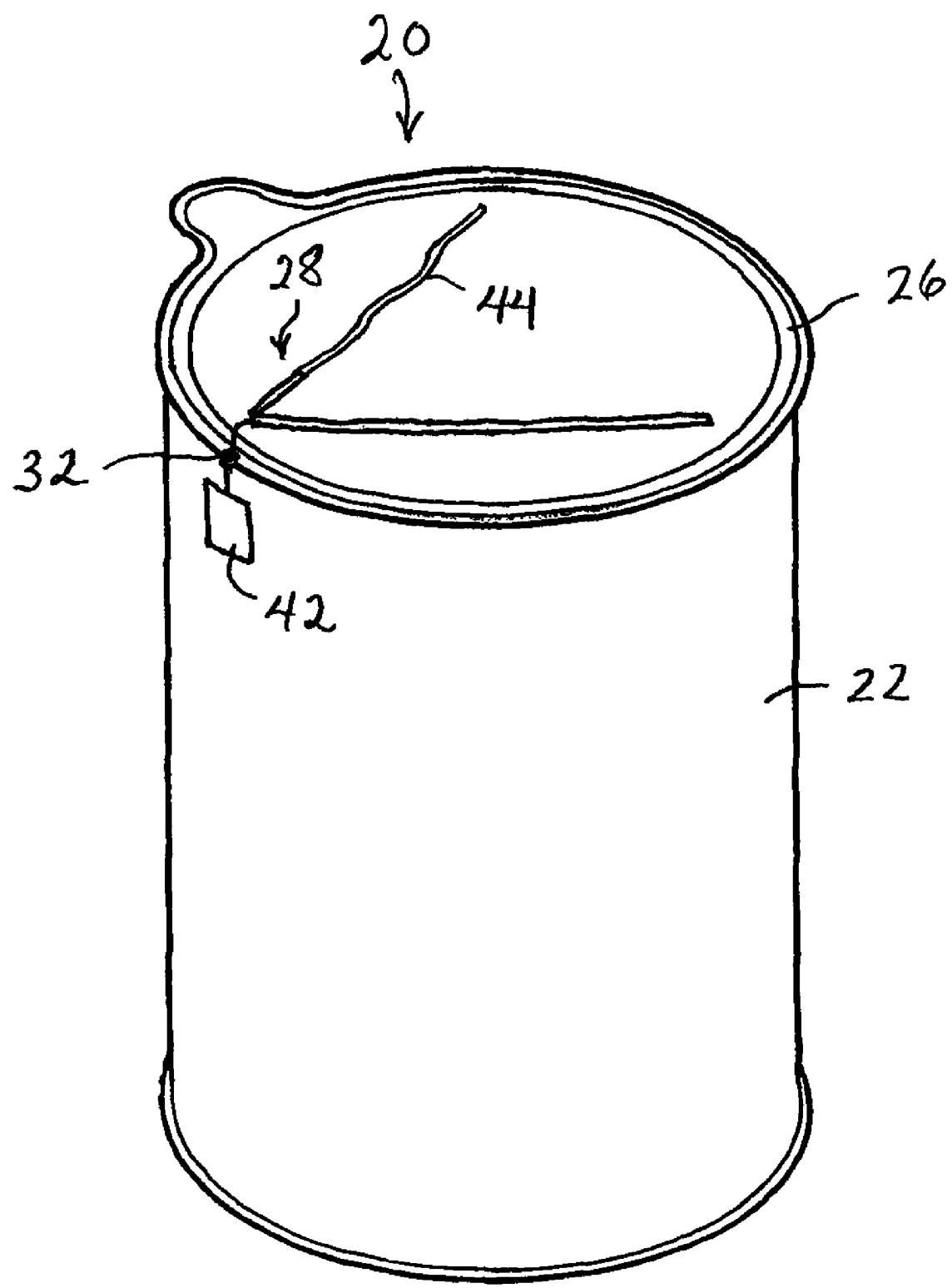
FIG. 3 shows a perspective view of a representative container, where the container includes a can and a removable lid, and the container is in a closed condition.
Figure 4:
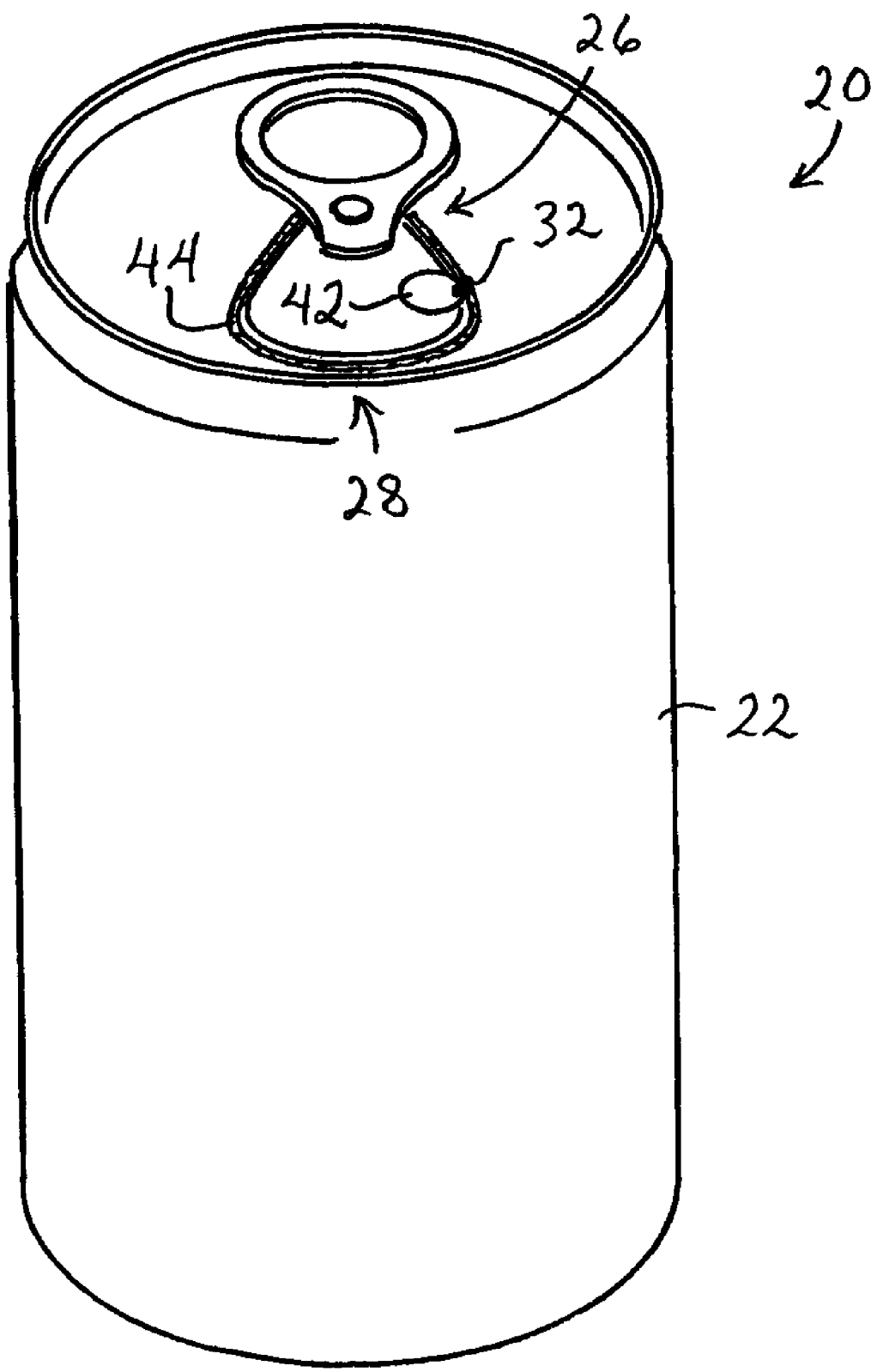
FIG. 4 shows a perspective view of a representative container which is in a closed condition, and where the container includes a can and another configuration of a removable lid.

With reference to FIGS. 3 and 4, the packaging system can have a container 22 which is configured to provide a can with a lid-opening region. The can has an access portion 26, which includes an access opening that is generally adjacent one end of the can, and a cooperating lid. Any operative lid configuration can be employed. Desirably, the can may have an easy-open lid that can be manually removed without the use of a tool, such as can opener. Thus, the lid can be initially installed to provide the desired, closed arrangement of the access portion, and can be removed to provide the desired, open arrangement of the access portion. The electronic data mechanism 28 can include a data memory portion 42 and a tag antenna portion 44. In a desired arrangement, the data mechanism can be a RFID tag. The data portion 42 can be connected to any operative section of the can container 22, and as representatively shown, the data portion may be positioned generally proximate the opening of the can container. The antenna portion 44 can be connected to the lid, and is appropriately sized and distributed to provide the desired antenna functionality. When the lid is installed, the antenna portion 44 operatively connects to the data portion 42 of the electronic data mechanism, and the electronic data mechanism can be configured in its enabled condition. When the lid is removed, antenna portion 44 operatively disconnects from the data portion 42 to thereby disable the ordinary operation electronic data mechanism.

Optionally, the antenna portion 44 of the electronic data mechanism 28 may be positioned on the main body of the can, and may extend along a region that is generally proximate the opening section of the can container. The data portion 42 can be connected to the lid. When the lid is installed, the antenna portion 44 operatively connects to the data portion 42 of the electronic data mechanism, and the electronic data mechanism can be configured in its enabled condition. When the lid is removed, the data portion 42 operatively disconnects from the antenna portion 44 to thereby disable or deactivate the ordinary operation of the electronic data mechanism.

Figure 5:
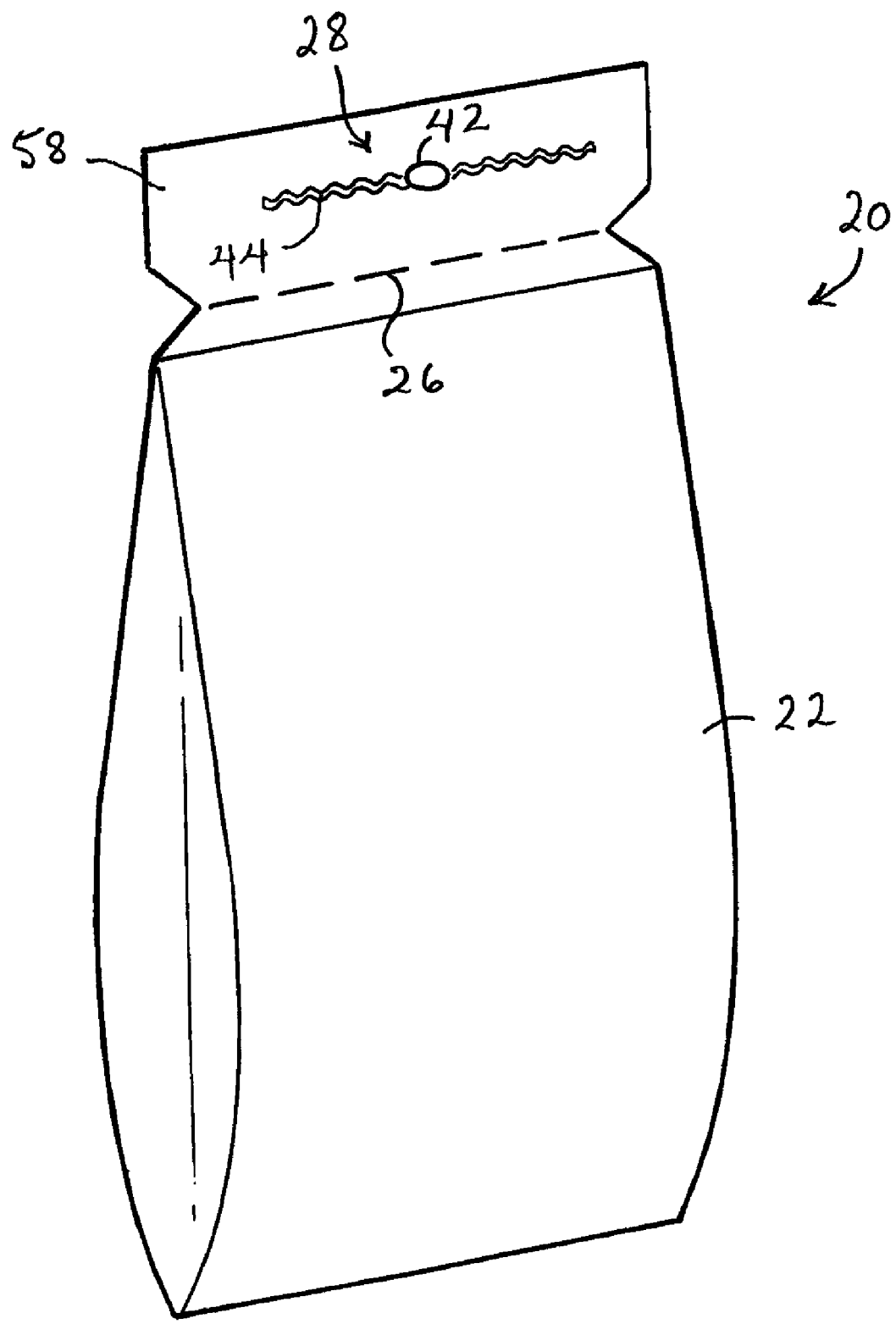
FIG. 5 shows a perspective view of a representative container, where the container is in a closed condition, and the container includes a pouch and a strip that can be removed to open the pouch.
Figure 6:
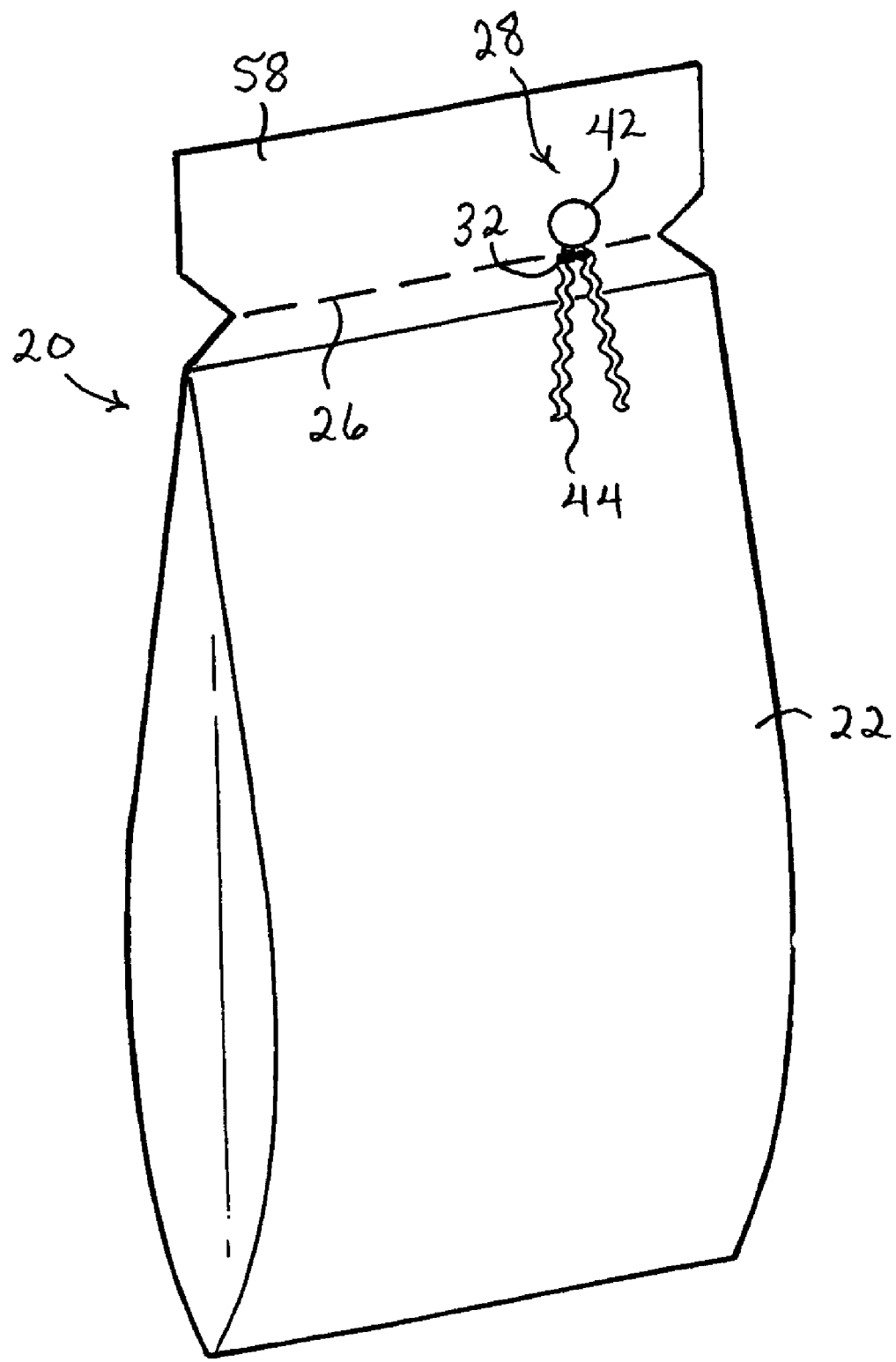
FIG. 6 shows a perspective view of a representative container, which is in a closed condition, and where the container includes a pouch and another configuration of a strip that can be removed to open the pouch.
Figure 7:
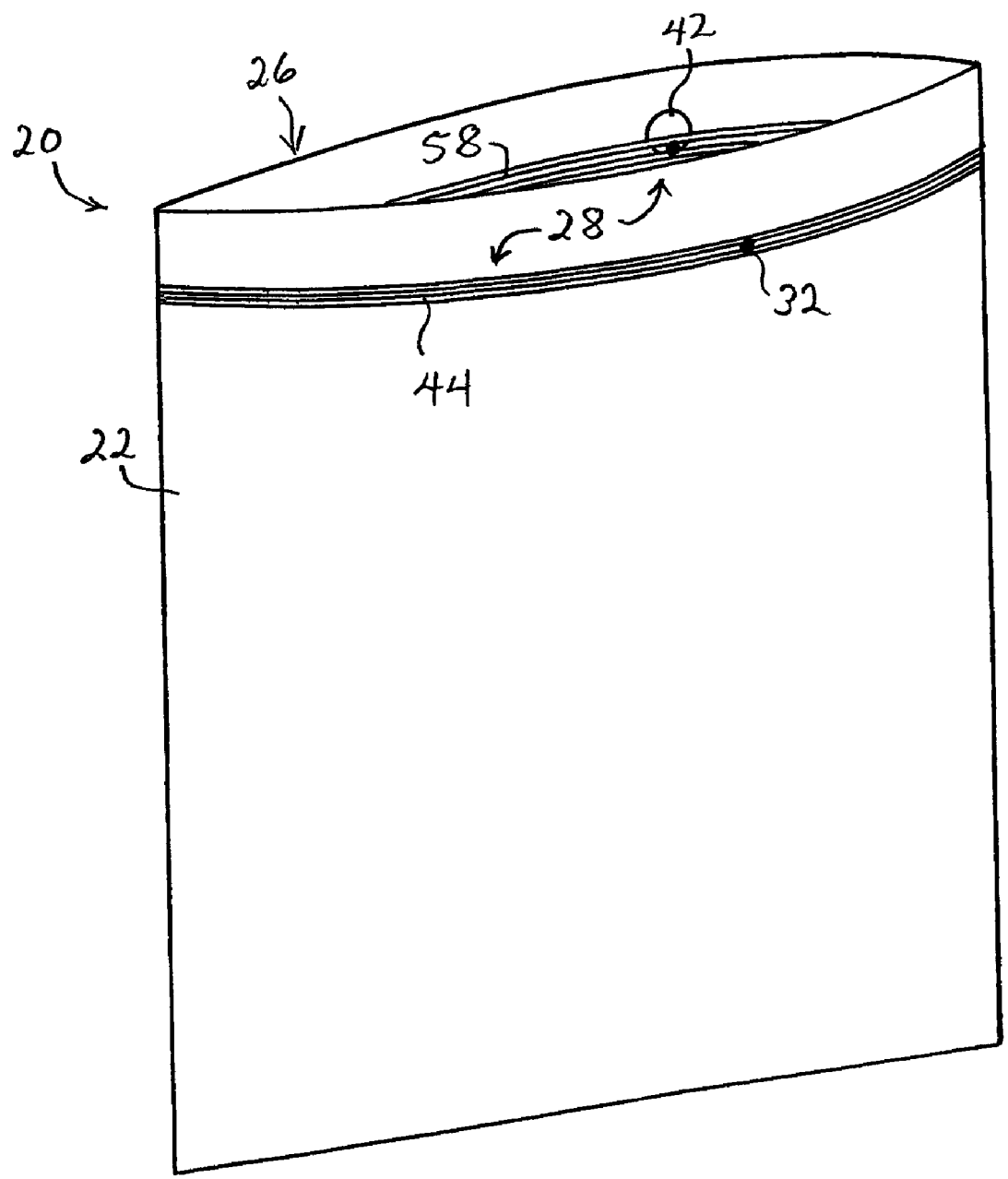
FIG. 7 shows a perspective view of a representative container, where the container is in an open condition, and the container includes a pouch and zipper mechanism that can be selectively moved to open and close the pouch.

With reference to FIGS. 5, 6 and 7, the packaging system can have a container 22 configured to provide a flexible pouch with an appointed opening region. The pouch has an access portion 26. As representatively shown, the access portion may include a cooperating strip-opening mechanism 58 that can be manipulated to provide an access opening that is positioned generally adjacent one end of the pouch. Any operative configuration of the strip-opening can be employed. For example, the pouch may have an easy-open tear-strip that can be manually removed without the use of a tool, such as a knife or scissors.

Alternatively, the strip-opening mechanism 58 may include a snap mechanism, a zipper mechanism, a clamp mechanism or the like, as well as combinations thereof. Thus, the opening-strip can be installed to provide the selected closed arrangement, and can be removed or otherwise manipulated to provide the selected open arrangement of the access portion. The electronic data mechanism 28 can include a data memory portion 42 and a tag antenna portion 44. In a desired arrangement, the data mechanism can be a RFID tag. A particular arrangement of the packaging system can have both the data portion 42 and antenna portion 44 attached to the opening-strip section of the pouch container (e.g. FIG. 5).

Alternatively, the antenna portion 44 can be positioned on the main body of the pouch container, and the data portion 42 can be connected to the strip-opening section of the pouch container (e.g. FIG. 6). When the opening-strip is installed or closed, the antenna portion 44 operatively connects to the data portion 42 of the electronic data mechanism, and the electronic data mechanism can be configured in its enabled condition. When the opening-strip is removed, the data portion 42 operatively disconnects from the antenna portion 44 to thereby disable or deactivate the ordinary operation of the electronic data mechanism.

Optionally, the data portion 42 can be positioned on the main body of the pouch container, and may be located generally proximate the intended opening of the pouch container. The antenna portion 44 can be connected to the strip-opening section of the pouch container. When the opening-strip is installed, the antenna portion 44 operatively connects to the data portion 42 of the electronic data mechanism, and the electronic data mechanism can be configured in its enabled condition. When the opening-strip is removed, the antenna portion 44 operatively disconnects from the data portion 42 to thereby disable or deactivate the ordinary operation of the electronic data mechanism.

With reference to FIG. 7, the pouch container can have a strip-opening mechanism 58 which includes a zipper mechanism that can be selectively operated to close, open and re-close the container a plurality of times. As representatively shown, the antenna portion 44 can be positioned on the main body of the pouch container, and the data portion 42 can be connected to the strip-opening section of the pouch container. Alternatively, the data portion 42 can be positioned on the main body of the pouch container, and the antenna portion may be located on the strip-opening section of the pouch container. The antenna portion 44 can be connected to the strip-opening section of the pouch container. When the zipper mechanism is closed, the antenna portion 44 operatively connects to the data portion 42 of the electronic data mechanism, and the electronic data mechanism can be configured in its enabled condition. When the zipper mechanism is opened, the data portion 42 operatively disconnects from the antenna portion 44 to thereby disable or deactivate the ordinary operation of the electronic data mechanism.

Figure 8:
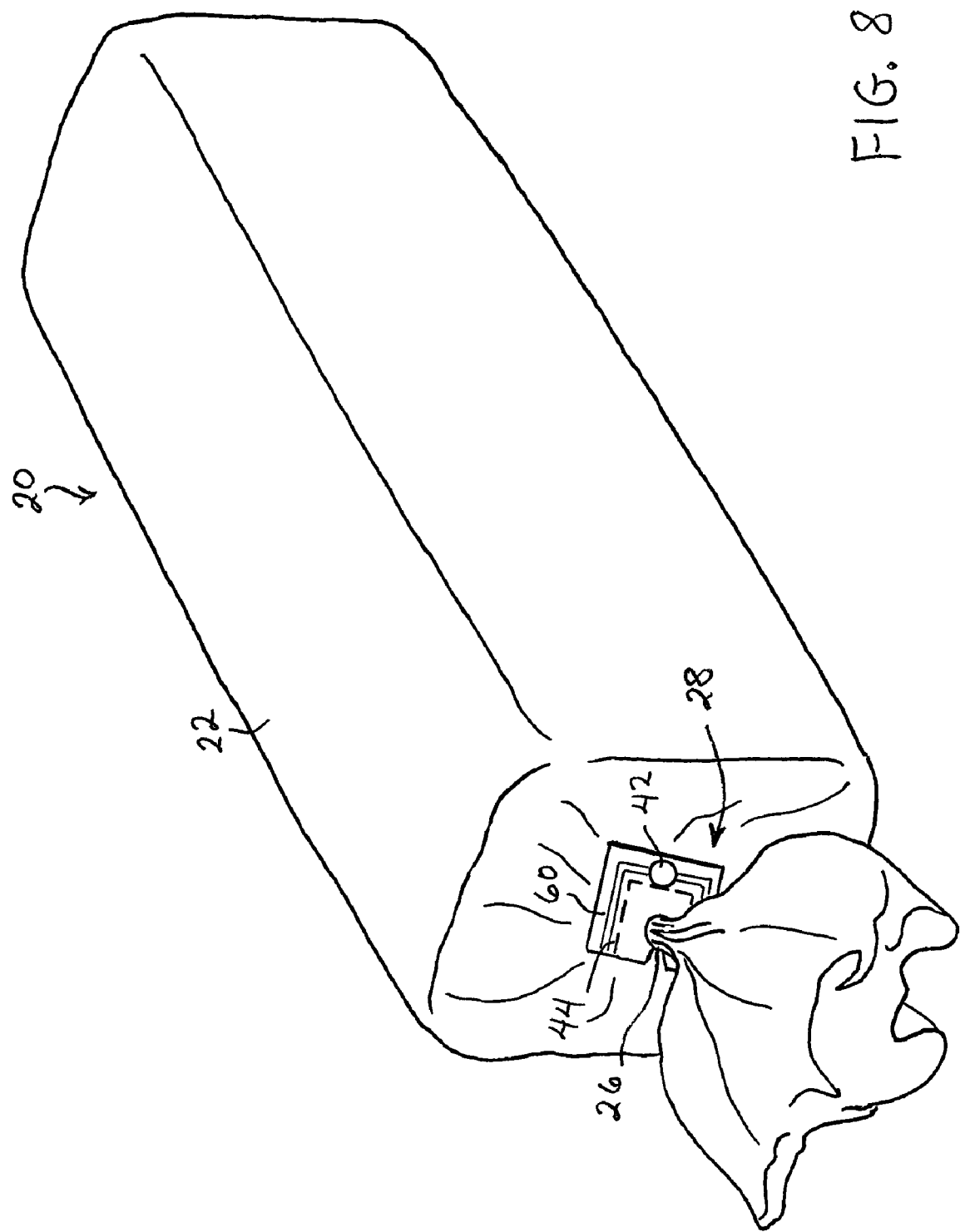
FIG. 8 shows a perspective view of a representative container, which includes a bag and a clip-closure mechanism that can be selectively moved to open and close the bag, and where the container is in a closed condition.
Figure 8A:
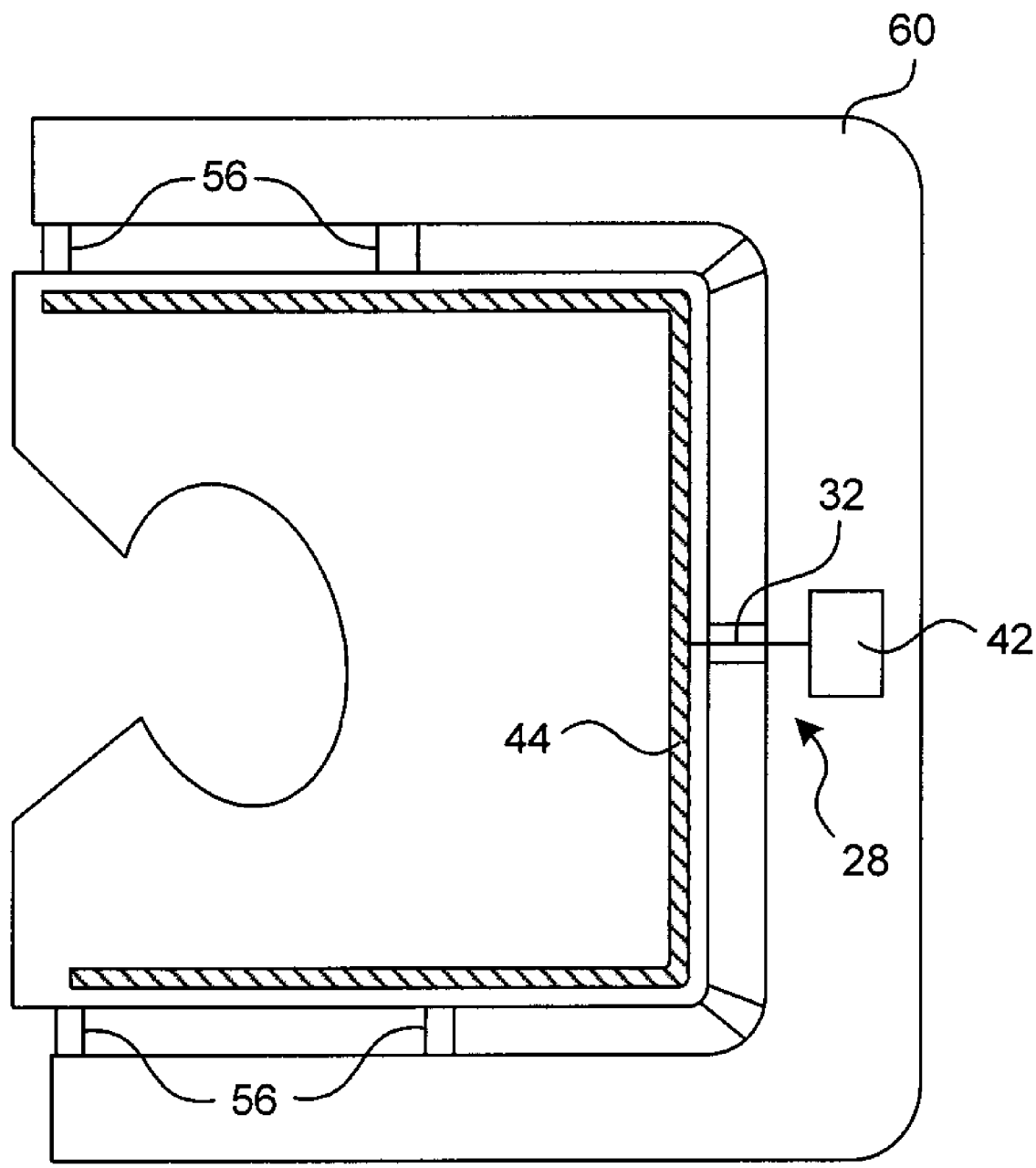
FIG. 8A shows a top, plan view of a representative clip-closure mechanism.

With reference to FIGS. 8 and 8A, the packaging system can have a container 22 configured to provide a flexible bag with an appointed opening region. The pouch has an access portion 26 which includes a cooperating clip-closure mechanism 60 that can be manually manipulated to provide an access opening. The access opening may, for example, be positioned generally adjacent one end of the bag. Any operative configuration of the clip-closure can be employed. Thus, the clip-closure 60 can be installed to provide the selective closed arrangement, and can be removed to provide the selective open arrangement of the access portion of the bag. The electronic data mechanism 28 can include a data memory portion 42 and a tag antenna portion 44, and in a desired arrangement, the data mechanism can be a RFID tag. A particular arrangement of the packaging system can have both the data portion 42 and antenna portion 44 attached to the clip-closure section of the packaging system. Another feature can have the clip-closure configured with a detachment mechanism 56 (e.g. FIG. 8A) which allows a selected separation of the data portion 42 and/or antenna portion 44 of the electronic data mechanism 28 from a main body of the clip-closure. For example, the detachment mechanism 56 can include a region of reduced strength and increased frangibility which can be readily broken by hand to provide the desired separation. As representatively shown, the data mechanism 28 can be connected to the clip-closure with a system of relatively low-strength, spaced-apart support members that can be manually broken by an ordinary person.

Figure 10:
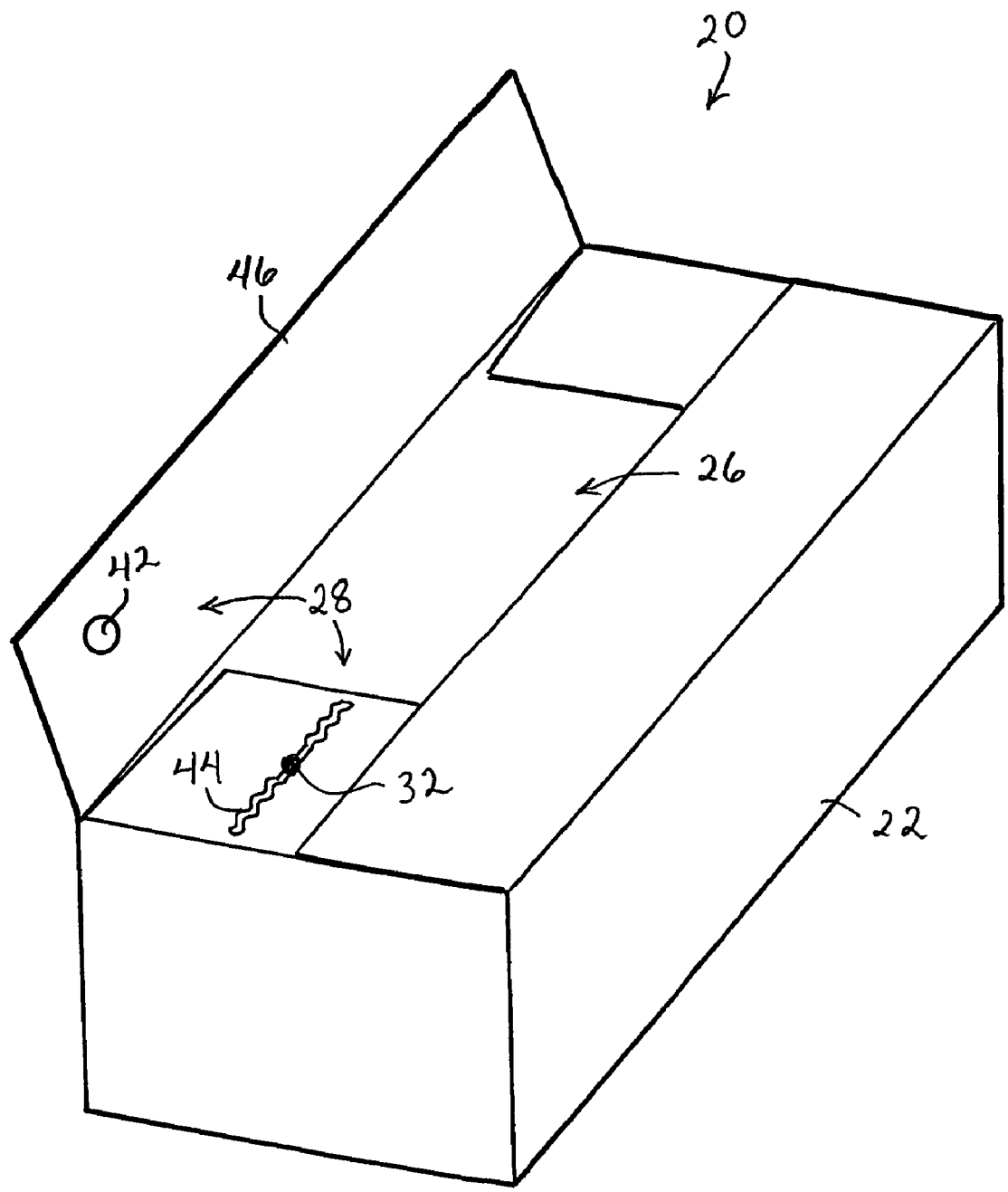
FIG. 10 shows a perspective view of a representative container where the container is in an open condition, and the container includes a box and another configuration of a flap-closure mechanism.
Figure 11:
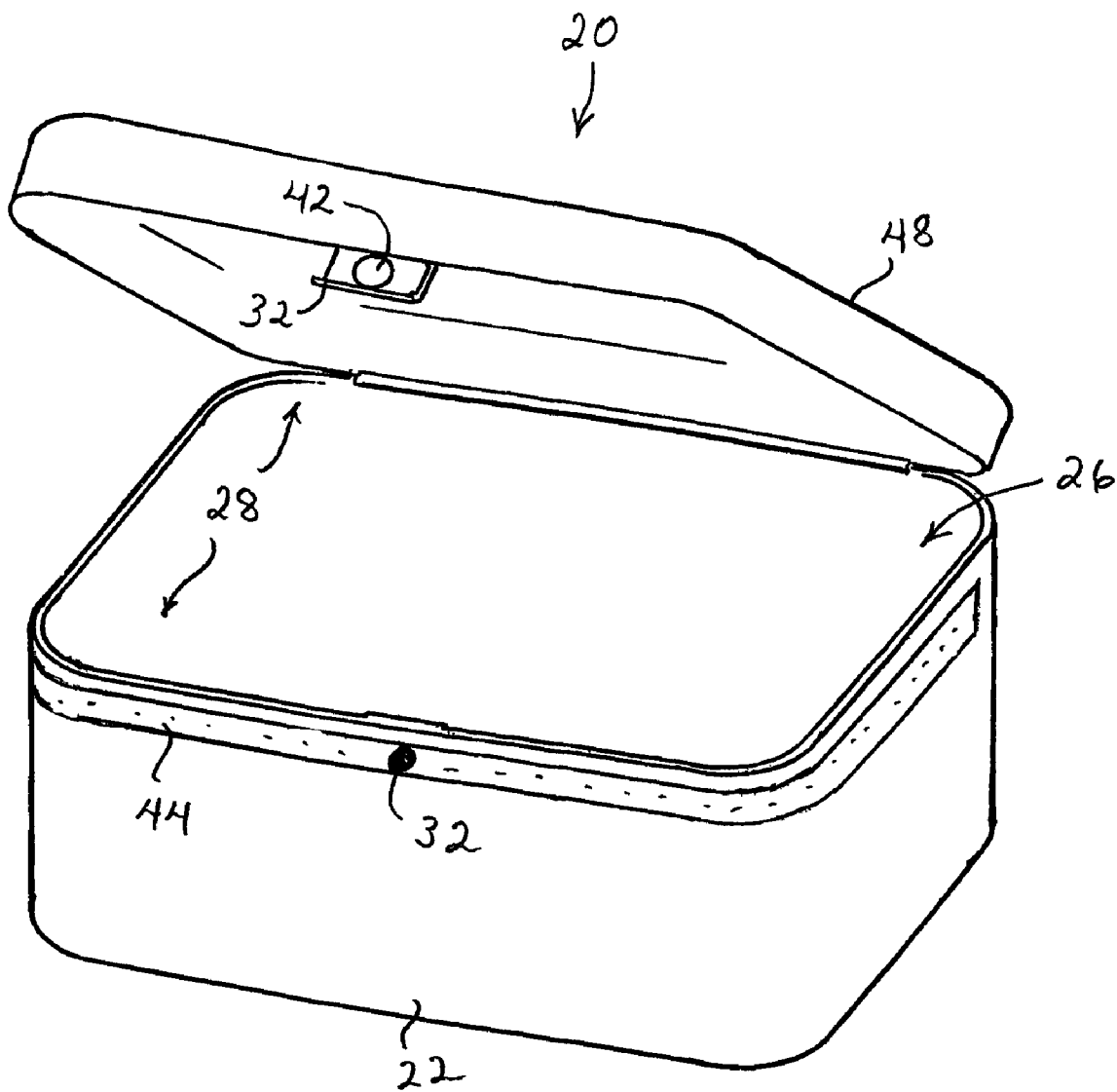
FIG. 11 shows a perspective view of a representative container which includes a box with a lid-closure mechanism, and where the container is in an open condition.

With reference to FIGS. 9-11, the packaging system can have a container 22 configured to provide a carton or box. The box material may be rigid, semi-rigid, flexible or combinations thereof. The box has an access portion 26 which can provide an access opening that is within, along or generally adjacent at least one face-panel of the box. The access portion can include a cooperating flap section 46 (e.g. FIGS. 9 and 10). For example, the flap 46 may be removably attached with an adhesive, and may be at least partially peeled away to provide access to contents within the box. Alternatively, the access portion 26 can include a cooperating lid section 48 (e.g. FIG. 11), and the lid section may be removably attached or pivotably attached to the main body of the box. Thus, the flap or lid section can be installed or otherwise positioned to provide the selected closed arrangement, and can be removed or otherwise repositioned to provide the selected open arrangement of the access portion 26. The electronic data mechanism 28 can include a data memory portion 42 and a tag antenna portion 44, and in a desired arrangement, the data mechanism can be a RFID tag. The data portion 42 can be connected to any operative section of the box container 22. As representatively shown in FIG. 9, the data portion may be attached to the main body of the box, and may be positioned generally proximate the opening section of the box. The antenna portion 44 can be connected to the flap or lid section of the box. The antenna portion may, for example, be configured to extend along a terminal, outer periphery of the flap or lid section of the box. When the flap or lid section is installed and closed, the antenna portion 44 operatively connects to the data portion 42 of the electronic data mechanism, and the electronic data mechanism can be configured in an enabled condition. When the flap or lid section is opened, antenna portion 44 operatively disconnects from the data portion 42 to thereby disable the previous, ordinary operation of the electronic data mechanism. When the flap or lid is reinstalled or replaced, the antenna portion 44 can operatively reconnect to the data portion 42 to thereby re-activate or otherwise re-enable the RFID tag or other electronic data mechanism to an intended operation.

As representatively shown in FIG. 11, the antenna portion 44 of the electronic data mechanism may alternatively be attached to the main body of the box, and the data storage portion 42 can be connected to the flap or lid section of the box. As representatively shown, the antenna portion may be configured to extend along a terminal, outer periphery of the opening section of the box. When the flap or lid section is installed and closed, the data portion 42 operatively connects to the antenna portion 44 of the electronic data mechanism, and the electronic data mechanism can be configured in an enabled condition. When the flap or lid section is opened, the data portion 42 operatively disconnects from the antenna portion 44 to thereby disable the previous, ordinary operation of the electronic data mechanism. When the cap is replaced, the antenna portion 44 operatively reconnects to the data portion 42 to thereby re-activate or otherwise re-enable the RFID tag or other electronic data mechanism to its intended operation.

Figure 12:
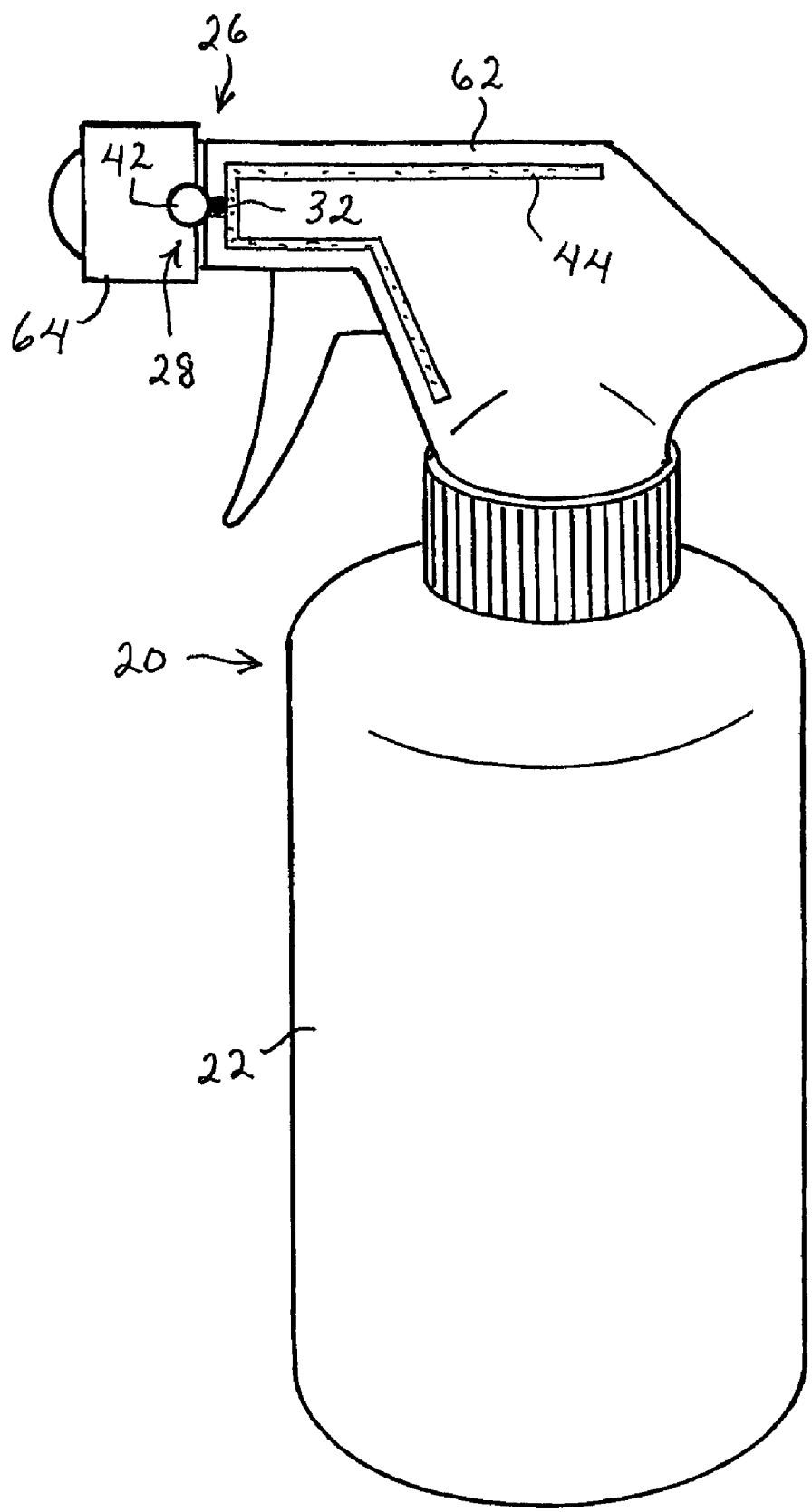
FIG. 12 shows a perspective view of a representative container which includes a bottle with a dispensing-nozzle mechanism that can be selectively moved to an open or closed condition.

With reference to FIG. 12, the packaging system can have a container 22 configured with a dispensing nozzle 62. For example, the packaging system can include a bottle with an access portion 26 that includes a spray nozzle. The spray nozzle provides an access opening that is generally adjacent one end of the bottle. In a desired feature, the nozzle can include a selector portion 64, which can be configured to provide the selective, closed arrangement, and the selective, open arrangement of the access portion. For example, the nozzle can be rotatably movable to provide the open and closed arrangements. The electronic data mechanism 28 can include a data memory portion 42 and a data antenna portion 44. In a desired arrangement, the data mechanism can be a RFID tag. The data portion 42 can be connected to any operative section of the bottle container 22 and nozzle 62. As representatively shown, the data portion may be attached to the main body of the nozzle or bottle, and positioned proximate the opening section of the bottle. The antenna portion 44 can be connected to the selector portion 64 of the nozzle, and appropriately configured to provide the desired antenna functionality. Optionally, the data portion may be attached to the selector portion 64 of the nozzle, and the antenna portion 44 may be connected to the main body of the nozzle or container. When the nozzle selector 64 is in a first (e.g. open or closed) position, the antenna portion 44 operatively connects to the data portion 42 of the electronic data mechanism, and the electronic data mechanism can be configured in an enabled condition. When the nozzle selector 64 is in a second (e.g. closed or open) position, the antenna portion 44 operatively disconnects from the data portion 42 to thereby disable the previous, ordinary operation of the electronic data mechanism. When the nozzle selector 64 cap is returned to its first position, the antenna portion 44 operatively reconnects to the data portion 42 to thereby re-activate or otherwise re-enable the RFID tag or other electronic data mechanism to its intended operation.

Those skilled in the art will recognize that the present method, apparatus or system is capable of many modifications and variations without departing from the scope thereof. Accordingly, the detailed description and examples set forth above are meant to be illustrative only and are not intended to limit, in any manner, the scope of the method and apparatus as set forth in the appended claims.

The invention claimed is:

1. An apparatus, comprising:
a container having an enclosure mechanism movable between an open position and a closed position; and
a data tag affixed to the container, the data tag having a first component and a second component, wherein the data tag is configured to communicate wirelessly at a first range if the first component is in a first position relative to the second component, and wherein the data tag is configured to communicate wirelessly at a second range smaller than the first range if the first component is in a second position relative to the second component,
wherein the first component is in the first position relative to the second component if the enclosure mechanism is in the closed position, and
wherein the first component is in the second position relative to the second component if the enclosure mechanism is in the open position.

2. The apparatus of claim 1 wherein the enclosure mechanism comprises a frangible member that is ruptured if the enclosure mechanism is moved from the closed position to the opened position.

3. The apparatus of claim 1 wherein the data tag comprises an antenna portion and a data memory portion, and wherein the antenna portion and data memory portion are operably separated when the data tag is in the second position.

4. The apparatus of claim 1 wherein the first component is moveable between the first position relative to the second component and the second position relative to the second component, and wherein the first component is further moveable between the second position relative to the second component and the first position relative to the second component.

5. The apparatus of claim 1 wherein the data tag is at least partially frangible.

6. The apparatus of claim 1 wherein the first component comprises a first antenna portion and the second component comprises a second antenna portion, wherein when the first antenna portion is in the first position relative to the second antenna portion the data tag is configured to communicate electronically using the first and second antenna portions together as a single antenna, and wherein when the first antenna portion is in the second position relative to the second antenna portion, the data tag is configured to communicate electronically using one of the first or second antenna portions, but not both the first and second antenna portions.

7. The apparatus of claim 6 wherein the first antenna portion and second antenna portion are frangibly connected when the first antenna portion is in the first position relative to the second antenna portion.

8. A system, comprising:
a container;
means for accessing configured to provide access to the container, wherein the means for accessing can be moved between a closed position and an open position; and
means for communicating electronically carried by the container and configured to communicate electronically with a reader mechanism, wherein the means for communicating electronically is configured to move between a first position if the means for accessing is in the closed position, and a second position if the means for accessing is in the open position, and wherein the means for communicating electronically is operative at a first range if in the first position, and at a second range smaller that the first range if in the second position.

9. The system of claim 8 wherein the means for communicating electronically is selectively movable between the first position and the second position.

10. The system of claim 8 wherein the means for communicating electronically is selectively movable between the second position and the first position.

11. The system of claim 8 wherein the means for communicating electronically can be moved from the first position to the second position, but cannot be moved from the second position to the first position.

12. The system of claim 8 wherein the means for communicating electronically is configured to communicate wirelessly.

* * * * *

UNITED STATES PATENT AND TRADEMARK OFFICE
CERTIFICATE OF CORRECTION

PATENT NO. : 8,318,111 B2
APPLICATION NO. : 13/006843
DATED : November 27, 2012
INVENTOR(S) : Mingerink et al.

Page 1 of 1

It is certified that error appears in the above-identified patent and that said Letters Patent is hereby corrected as shown below:

On the Title Page, in Item (56), under "OTHER PUBLICATIONS", in Column 2, Line 1,
delete "Karjoth, G. And Moskowitz, P., "Disabling Rfid Tages with Visible" and
insert -- Karjoth, G. and Moskowitz, P., "Disabling RFID Tags with Visible --, therefor.

In the Specifications

In Column 3, Line 33, delete "electronic data mechanism 30" and
insert -- electronic data mechanism 28 --, therefor.

In the Claims

In Column 16, Line 33, in Claim 8, delete "that" and insert -- than --, therefor.

Signed and Sealed this
Fourth Day of June, 2013

Teresa Stanek Rea
*Acting Director of the United States Patent and Trademark Office*